(12) United States Patent
Prakash et al.

(10) Patent No.: US 6,225,493 B1
(45) Date of Patent: May 1, 2001

(54) METAL ION ASSISTED N-[N-(3,3-DIMETHYLBUTYL)-L-α-ASPARTYL]-L-PHENYLALANINE 1-METHYL ESTER ISOMER RESOLUTION

(75) Inventors: Indra Prakash, Hoffman Estates; Joseph P. Haar, Jr., Edwardsville; Robert Y. Zhao, Mount Prospect, all of IL (US)

(73) Assignee: The Nutrasweet Company, Chicago, IL (US)

( * ) Notice: Subject to any disclaimer, the term of this patent is extended or adjusted under 35 U.S.C. 154(b) by 0 days.

(21) Appl. No.: 09/641,976

(22) Filed: Aug. 21, 2000

(51) Int. Cl.[7] .................................................. C07C 229/00
(52) U.S. Cl. ................................................................ 560/40
(58) Field of Search ............................... 560/40; 562/455; 564/304

(56) References Cited

U.S. PATENT DOCUMENTS

| | | | |
|---|---|---|---|
| 5,432,262 | * | 7/1995 | Takemoto et al. .................... 530/344 |
| 5,501,712 | * | 3/1996 | Abe et al. ........................... 23/295 R |
| 5,591,886 | * | 1/1997 | Ichiki et al. ............................ 560/41 |
| 5,693,485 | * | 12/1997 | Harada et al. ....................... 435/68.1 |
| 5,728,862 | * | 3/1998 | Prakash ................................. 560/40 |
| 6,008,403 | * | 12/1999 | Katsuura et al. ....................... 560/40 |

* cited by examiner

*Primary Examiner*—Joseph K. McKane
*Assistant Examiner*—Joseph Murray
(74) *Attorney, Agent, or Firm*—Fitzpatrick, Cella, Harper & Scinto

(57) ABSTRACT

This invention relates to the purification of N-[N-(3,3-dimethylbutyl)-L-α-aspartyl]-L-phenylalanine 1-methyl ester by resolving a mixture of the alpha- and beta-isomers of N-[N-(3,3-dimethylbutyl)-L-α-aspartyl]-L-phenylalanine 1-methyl ester using metal ions.

9 Claims, No Drawings

METAL ION ASSISTED N-[N-(3,3-DIMETHYLBUTYL)-L-α-ASPARTYL]-L-PHENYLALANINE 1-METHYL ESTER ISOMER RESOLUTION

BACKGROUND OF THE INVENTION

1. Field of the Invention

This invention relates to the purification of N-[N-(3,3-dimethylbutyl)-L-α-aspartyl]-L-phenylalanine 1-methyl ester (α-neotame) by resolution of the isomers of neotame.

2. Related Background Art

N-[N-(3,3-dimethylbutyl)-L-α-aspartyl]-L-phenylalanine 1-methyl ester (α-neotame) is a high potency dipeptide sweetener (about 8000× sweeter than sucrose) that has the formula

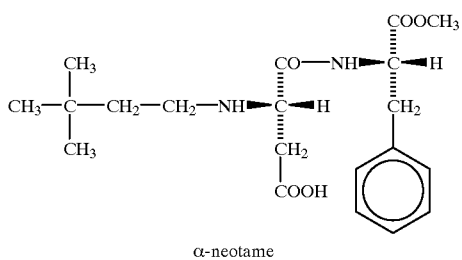

α-neotame

Its β-isomer, N-[N-(3,3-dimethylbutyl)-L-β-aspartyl]-L-phenylalanine 1-methyl ester (β-neotame), has the structure

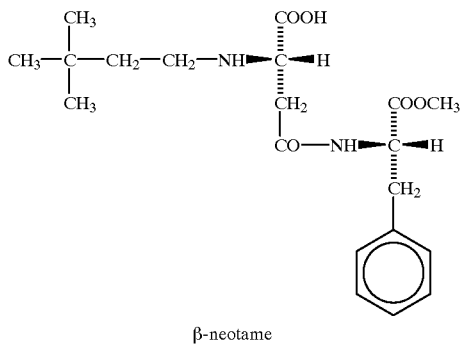

β-neotame

The chemical synthesis of α-neotame is disclosed in U.S. Pat. No. 5,480,668, U.S. Pat. No. 5,510,508 and U.S. Pat. No. 5,728,862, the disclosure of each of which is incorporated by reference herein. U.S. Pat. Nos. 5,510,508 and 5,728,862 describe the conventional synthesis of α-neotame by hydrogenation of a mixture of aspartame and 3,3-dimethylbutyraldehyde with a catalyst such as Pd on carbon.

A number of other synthetic routes to neotame have been explored. Certain of these routes, for example, the coupling of phenylalanine methyl ester to neo-aspartic anhydride as disclosed in U.S. Pat. No. 6,077,962, and methods which employ Z-aspartame (α- and β-mixture) as a starting material, as disclosed in U.S. Pat. No. 5,302,743 and JP 60-075497, do not yield pure α-neotame. In fact, both the desired α-isomer and the undesirable β-isomer of neotame are obtained. Since α-neotame is mainly employed in foods for human consumption, it is extremely important that α-neotame exist in a highly purified state. Thus, it is clear that there is a need for a purification strategy which selectively produces the pure α-isomer of neotame.

SUMMARY OF THE INVENTION

This invention is directed to a process of purifying N-[N-(3,3-dimethylbutyl)-L-α-aspartyl]-L-phenylalanine 1-methyl ester (α-neotame) comprising the steps of providing a mixture of (i) the α- and β-isomers of neotame and (ii) an organic solvent; contacting the mixture with aqueous metal ion such that the β-isomer chelates the metal ion and forms a metal complex; and partitioning the metal complex from the α-isomer of neotame.

DETAILED DESCRIPTION

The present invention is directed to a purification scheme for N-[N-(3,3-dimethylbutyl)-L-α-aspartyl]-L-phenylalanine 1-methyl ester (α-neotame). The purification scheme of the present invention is particularly suitable for use when neotame is produced by any method which results in the coexistence of both the α- and β-isomers of neotame.

According to the present invention, a mixture of the α- and β-isomers of neotame in an organic solvent is contacted with aqueous metal ion such that the β-isomer chelates the metal ion and forms a metal complex; the metal complex is then partitioned from the α-isomer of neotame. In effect, the separation is between a complex of one isomer and the zwitterionic form of the other isomer.

According to the first step of the present invention, a mixture of (i) the α- and β-isomers of neotame and (ii) an organic solvent is provided.

The mixture can take the form of a reaction mixture in which neo-aspartic anhydride was coupled with phenylalanine methyl ester or a reaction mixture in which Z-aspartame (mixture of α- and β-aspartame) was employed to form neotame. Alternatively, the mixture can be formed by adding an organic solvent to such a reaction mixture or to a dry mixture of the α- and β-isomers of neotame.

Any organic solvent which has a different degree of solvation power for the metal complex of the β-isomer and the α-isomer of neotame is suitable for use in the present invention. Suitable organic solvents include, without limitation, glycerol, toluene, chloroform, dichloromethane, butyl acetate, ethyl acetate and mixtures thereof. One of ordinary skill in the art will readily appreciate that the greater the difference between the solubilities of the metal complex of the β-isomer and the α-isomer of neotame in a given solvent, the more useful the solvent will be for purposes of the present invention.

According to the second step of the present invention, the mixture is contacted with aqueous metal ion such that the β-isomer of neotame chelates the metal ion to form a metal complex. Suitable metal ions include, without limitation, $Cu^{2+}$, $Zn^{2+}$, $Fe^{2+}$, $Fe^{3+}$, $Mn^{2+}$, $Ca^{2+}$ and $Mg^{2+}$. Preferably the metal ion is $Cu^{2+}$. One of ordinary skill in the art will readily appreciate that any metal ion capable of forming a metal complex with the β-isomer of neotame is suitable for use in the present invention. Typically a 1–2 equivalent amount, and preferably an equimolar amount, of metal ion is used as compared to the amount of β-isomer present.

Typically, contacting the mixture with aqueous metal ion is accomplished by adding to the mixture of the α- and β-isomers an aqueous solution containing a metal salt such as a sulfate, chloride or nitrate dissolved therein.

After addition of the metal ion to the solution, the pH is optionally but preferably manipulated to be in a range from about 2 to about 9, more preferably from about 3 to about 8, and most preferably from about 4 to about 7. The formation of a metal complex of the β-isomer of neotame is maximized at these pH conditions. Typically, the pH is manipulated by the addition of an acid, a base or both.

Simultaneously with the formation of the metal complex of the β-isomer, a biphasic system comprising an aqueous layer and an organic layer is created. The organic layer primarily contains the metal complex of the β-isomer of neotame, while the aqueous layer primarily contains the α-isomer of neotame.

According to the third step of the present invention, the metal complex is partitioned from the α-isomer of neotame.

Partitioning may be achieved by any known means, including, without limitation, liquid/liquid extraction, solid/liquid extraction and chromatography. One of ordinary skill in this art will readily appreciate that the metal complex may exist as a solid or in solution, depending upon the organic solvent used, the purification conditions, etc. Likewise, one of ordinary skill in this art will readily appreciate that the α-isomer exists in solution at this point. If liquid/liquid extraction is to be carried out, i.e., both the metal complex and the α-isomer are in solution, a simple separatory funnel, continuous extractor or counter-current device may be employed. If chromatography is to be used, any stationary phase/solvent combination which enables resolution of the α-isomer is suitable.

After partitioning the metal complex from the α-isomer, the aqueous solution containing the α-isomer may optionally be acidified. Preferably, a pH of about 2–3 is achieved in such a step. This acidification step is typically accomplished by adding an acid to the aqueous solution containing α-neotame and aids in the purification of the α-neotame.

After partitioning the metal complex from the α-isomer, the α-isomer solution can be treated in order to form neotame crystals. Optionally, the solution may be concentrated or further processed and then treated such that α-neotame crystals form. Such treatments include, without limitation, the addition of water or the addition of another solvent which causes α-neotame crystals to form. Furthermore, other additives which facilitate the formation of α-neotame crystals may be added. An example of such an additive is α-neotame seed crystals. Additionally, the treatments may include the selection and maintenance of an appropriate temperature or temperature range at which to conduct the treatments. Optionally the treatments may also include the selection and maintenance of an appropriate pH or pH range at which to conduct the treatments.

The Examples which follow are intended as an illustration of certain preferred embodiments of the invention, and no limitation of the invention is implied.

EXAMPLE 1

The α-isomer of neotame (2.7 mmol, 1.0 g) and the β-isomer of neotame (0.90 mmol, 0.33 g) were combined dry. Glycerol (20% aqueous wt/wt) was added to the peptides to form a suspension. Hexane (12.5 ml) and ethyl acetate (33 ml) were added to the suspension. The mixture was stirred as 1M aqueous copper sulfate (0.9 mmol, 0.9 ml) was added. The pH was adjusted to 5 with 1M aqueous sodium hydroxide. A clear, biphasic system developed. By HPLC, the α:β ratio for the aqueous layer was determined to be 14.3:1. The α:β ratio for the organic layer was 2.27:1.

EXAMPLE 2

The α-isomer of neotame (2.7 mmol, 1.0 g) and the β-isomer of neotame (2.7 mmol, 1.0 g) were dissolved in methanol (10 ml). Water was added to the resulting solution. Butyl acetate (25 ml) was added to the mixture, followed by 1M aqueous copper sulfate (2.7 mmol, 2.7 ml). The pH was adjusted to 6 with 1M aqueous sodium hydroxide. A clear, biphasic system developed. By HPLC, the α:β ratio for the aqueous layer was determined to be 9.75:1. The α:β ratio for the organic layer was 0.876:1. To this system was added more methanol (5 ml). The solids were repartitioned, and no β-isomer was detected in the aqueous layer, while the organic layer α:β was 0.9:1.

EXAMPLE 3

In a Parr bottle containing a solution of Z-aspartame (α:β 3:1, 4.0 g, 9.34 mmol), 3,3-dimethylbutyraldehyde (1.18 ml, 9.40 mmol), methanol (50 ml), water (10 ml) and 0.25 g Pd/C (4% palladium on carbon, 50% wet) was added. After stirring for 5 minutes, the mixture was hydrogenated at 100 psi at room temperature for 4 hours. The mixture was filtered through a Celite bed, and the bed was washed with methanol (60 ml). The filtrate and washings were combined and concentrated. The mixture was dissolved in 200 ml 0.2 M copper sulfate/ethyl acetate/methanol (10:9:1). The pH was adjusted to 5.0–6.0 by the addition of 1.0 M aqueous sodium hydroxide. After separation, the organic layer was extracted with water (2×30 ml). The aqueous layer was extracted with ethyl acetate (2×30 ml). The organic layer contained β-neotame, and the aqueous layer contained α-neotame.

The aqueous layers which contained α-neotame were combined and acidified with 1.0 M hydrochloric acid to pH 3.0 and extracted again with ethyl acetate (4×30 ml). The extracted organic layers were dried over anhydrous magnesium sulfate, filtered, concentrated, and crystallized from ethanol/hexane. Pure (99% by HPLC) α-neotame (1.35 g, 51% yield) was obtained.

The $Cu^{++}$ chelated β-neotame in organic layers was combined and concentrated. The residue was dissolved in 10 ml of 1:1 methanol/sodium phosphate (1.0 M, pH 8.0). The precipitate was removed by centrifugation. The supernatant was concentrated, acidified to pH 3.0 with 1.0 M hydrochloric acid and extracted with ethyl acetate (3×15 ml). The ethyl acetate extracts were dried over anhydrous magnesium sulfate, filtered, concentrated, and crystallized from ethanol/hexane. α-Neotame (0.52 g, 58%), which contained 5% α-neotame by HPLC, was obtained.

EXAMPLE 4

To a mixture of α-neotame (3 g) and β-neotame (1 g) in 45 ml ethyl acetate was added 50 ml of a 250 mM aqueous solution of zinc chloride and 5 ml of methanol. Then the pH of the mixture was adjusted to about 6.0–6.5 with 100 mM aqueous sodium hydroxide. After separation, the organic layer was extracted with water (2×30 ml). The aqueous layer was extracted with ethyl acetate (2×30 ml). The organic layer contained β-neotame, and the aqueous layer contained α-neotame.

The aqueous layers which contained α-neotame were combined and acidified with 1.0 M hydrochloric acid to pH 3.0 and extracted again with ethyl acetate (4×30 ml). The extracted organic layers were dried over anhydrous magnesium sulfate, filtered, concentrated, and crystallized from ethanol/hexane. Pure (>98% by NMR) α-neotame (1.95 g, 65% yield) was obtained.

The $Zn^{++}$ chelated β-neotame in organic layers was combined and concentrated. The residue was dissolved in 20 ml of 1:1 methanol/sodium phosphate (1.0 M, pH 9.0). The precipitate was removed by centrifugation. The supernatant was concentrated, acidified to pH 3.0 with 1.0 M hydrochloric acid and extracted with ethyl acetate (3×20 ml). The ethyl acetate extracts were dried over anhydrous magnesium sulfate, filtered, concentrated, and crystallized from ethanol/hexane. β-Neotame (0.54 g, 54%), which contained 5–10% α-neotame by NMR, was obtained.

Other variations and modifications of this invention will be obvious to those skilled in this art. This invention is not to be limited except as set forth in the following claims.

What is claimed is:

1. A process of purifying N-[N-(3,3-dimethylbutyl)-L-α-aspartyl]-L-phenylalanine 1-methyl ester comprising the steps of:

providing a mixture of (i) the α- and β-isomers of N-[N-(3,3-dimethylbutyl)-L-α-aspartyl]-L-phenylalanine 1-methyl ester and (ii) an organic solvent;

contacting the mixture with aqueous metal ion, whereby the β-isomer of N-[N-(3,3-dimethylbutyl)-L-α-aspartyl]-L-phenylalanine 1-methyl ester chelates the metal ion to form a metal complex; and partitioning the metal complex from the α-isomer of N-[N-(3,3-dimethylbutyl)-L-α-aspartyl]-L-phenylalanine 1-methyl ester.

2. The process according to claim 1, wherein the organic solvent is selected from the group consisting of glycerol, toluene, chloroform, dichloromethane, butyl acetate, ethyl acetate and mixtures thereof.

3. The process according to claim 1, wherein the metal ion is selected from the group consisting of $Cu^{2+}$, $Zn^{2+}$, $Fe^{2+}$, $Fe^{3+}$, $Mn^{2+}$, $Ca^{2+}$ and $Mg^{2+}$.

4. The process according to claim 3, wherein the metal ion is $Cu^{2+}$.

5. The process according to claim 1, wherein the aqueous metal ion is supplied in the form of an aqueous solution of metal sulfate, metal chloride, or metal nitrate.

6. The process according to claim 1, wherein the pH of the mixture is from about 2 to about 9 after the contacting step.

7. The process according to claim 6, wherein the pH of the mixture is from about 3 to about 8 after the contacting step.

8. The process according to claim 7, wherein the pH of the mixture is from about 4 to about 7 after the contacting step.

9. The process according to claim 1, wherein the partitioning step comprises a method selected from liquid/liquid extraction, solid/liquid extraction and chromatography.

* * * * *

UNITED STATES PATENT AND TRADEMARK OFFICE
CERTIFICATE OF CORRECTION

PATENT NO. : 6,225,493 B1
DATED : May 1, 2001
INVENTOR(S) : Indra Prakash et al.

Page 1 of 1

It is certified that error appears in the above-identified patent and that said Letters Patent is hereby corrected as shown below:

Column 4,
Line 38, "$\alpha$-Neotame" should read -- $\beta$-Neotame --.

Signed and Sealed this

Fifth Day of March, 2002

Attest:

JAMES E. ROGAN
*Attesting Officer*     *Director of the United States Patent and Trademark Office*